United States Patent [19]

Orchard

[11] Patent Number: 4,668,564
[45] Date of Patent: May 26, 1987

[54] HYDROGEL MATERIALS FOR HOT AND COLD THERAPY AND METHOD FOR FORMING SAME

[75] Inventor: Lewis P. Orchard, Waco, Tex.

[73] Assignee: Spenco Medical Corporation, Waco, Tex.

[21] Appl. No.: 824,492

[22] Filed: Jan. 31, 1986

Related U.S. Application Data

[63] Continuation-in-part of Ser. No. 813,438, Dec. 26, 1985.

[51] Int. Cl.⁴ ............... B32B 27/40; B29C 67/00; A61L 15/00; A61K 9/00
[52] U.S. Cl. ................... 428/246; 128/156; 264/46.4; 428/304.4; 428/308.4; 428/316.6; 604/369; 604/897
[58] Field of Search ............ 128/155, 156; 428/68, 428/71, 76, 304.4, 306.6, 316.6, 246, 308.4; 524/767; 604/368, 369, 890, 896, 897; 264/46.4; 427/373

[56] References Cited

U.S. PATENT DOCUMENTS

| | | | |
|---|---|---|---|
| 3,674,027 | 7/1972 | Fleischmajer | 604/304 |
| 3,847,722 | 11/1974 | Kistner | 428/76 |
| 4,341,207 | 7/1982 | Steer et al. | 128/156 |
| 4,349,494 | 9/1982 | Fulmer | 264/46.4 |
| 4,353,955 | 10/1982 | Cook | 264/46.4 |
| 4,355,021 | 10/1982 | Kuy | 424/20 |
| 4,362,841 | 12/1982 | Minatona et al. | 128/156 |
| 4,377,160 | 3/1983 | Romaine | 128/156 |
| 4,383,079 | 5/1983 | Gasper et al. | 524/767 |
| 4,404,296 | 9/1983 | Shapel | 523/122 |
| 4,423,099 | 12/1983 | Mueller et al. | 428/306.6 |
| 4,425,917 | 1/1984 | Kuznetz | 128/403 |
| 4,452,892 | 6/1984 | Rosevear | 435/176 |
| 4,517,326 | 5/1985 | Cordts et al. | 524/310 |
| 4,530,220 | 7/1985 | Nambu et al. | 128/403 |
| 4,556,055 | 12/1985 | Bonner, Jr. | 128/402 |

Primary Examiner—William J. Van Balen
Attorney, Agent, or Firm—Donald L. Traut; Jeremiah J. Duggan

[57] ABSTRACT

A hot or cold compress a layer of substituted urea/urethane hydrogel material bonded to a porous substrate. The hydrogel material is made up of a high molecular weight polyol, a toluene diisocyanate prepolymer and water. Generally, the water and polyol each comprises between about 40 to 50% by weight of the hydrogel, with the diisocyanate prepolymer making up the remaining 12–16% by weight. The hot or cold compresses of the present invention are formed by preparing the hydrogel material and then placing a porous substrate in contact with the hydrogel prior to the time that gel formation is complete. In this manner, the hydrogel becomes integrally bonded to the porous substrate. Other materials such as terrycloth can be bonded to the porous substrate prior to bonding the substrate to the hydrogel. Articles useful in therapy can then be formed by attaching the edges of the cloth/porous substrate to form the desired object.

45 Claims, No Drawings

HYDROGEL MATERIALS FOR HOT AND COLD THERAPY AND METHOD FOR FORMING SAME

This application is a continuation in part of copending application Ser. No. 813,438 filed Dec. 26, 1985.

TECHNICAL FIELD

The present invention relates to objects having a soft hydrogel material incorporated therein and methods for forming same. The hydrogel material comprises a substituted urea/urethane material which imparts a high degree of thermal efficiency to the objects formed therefrom. That is, such objects possess the desirable property of remaining hot or cold for extended periods of time. Additionally, the present invention relates to a method for bonding a sheet of porous substrate material to the hydrogel material.

BACKGROUND ART

Various thermoelastomeric materials have been used in the past to impart desirable heat or cold retaining properties to objects, such as hot and cold compresses and disposable ice packs. Such materials have included, for example, substituted urea/urethane hydrogels. These hydrogels are quite soft and pliable, yet are capable of remaining hot or cold for extened periods of time. Unfortunately, the useful life of such gel containing objects is usually quite short. Further, such prior devices have the gelled material enclosed or confined in a pouch or bag.

The hydrogen material itself generally is prepared by mixing effective amounts of a polyalcohol (polyol) with a diisocyanate-capped prepolymer followed by the addition of water. The mixture is then poured into an appropriate mold where gel formation will occur spontaneouslyin a short period of time. Although much of the carbon dioxide gas which is liberated as a by-product of the water and isocyanate reaction escapes from the mixture prior to gel formation, a froth of carbon dioxide gas interspersed in the gel often remains at the uppermost surface of the gel. This is particularly true when the ratio of the surface area to the volume of the mold used is small. Although this froth does ot seriously impair the qualities of the hydrogel, it is unsightly and less desirable than a gel having a more uniform consistency.

Preparation of objects incorporating the above noted hydrogel material has been most commonly effected by placing the premolded hydrogel material in an envelope or pouch of cloth, plastic or other material and then sealing the open end of the envelope or pouch. The hydrogel material incorporated into objects so prepared, although having the desired thermal efficiency, often slips or shifts within the confines of its compartment because no satisfactory method for adhering the hydrogel to the covering material exists. Placing the formed hydrogel material within the envelope or pouch requires an additional step, and therefore additional cost, in the production of such objects. Further, placing a covering completely around the hydrogel material reduces the therapeutic capability of the gel by insulating it from the skin when in use in hot or cold therapy. A need exists, therefore, for a method of bonding hydrogel materials directly to a covering material. Further, a need exists for a more efficient way of making articles incorporating such hydrogels for hot and cold therapy purposes.

SUMMARY OF THE INVENTION

In accordance with the present invention, a method is provided for bonding a sheet of a porous substrate material, e.g., a substantially open-celled from, to a substituted urea/urethane hydrogel material. The method comprises contacting the sheet of porous substrate with the hydrogel material prior to the time that such hydrogel material has completely gelled or thickened. This can be accomplished by placing the sheet or porous substrate over the top of a mold into which the hydrogel mixture has been introduced, prior to the time that such mixture has completely gelled. Preferably, the sheet of porous substrate is contacted with the hydrogel mixture in the mold within approximately thirty (30) seconds from the time that such hydrogel material was introduced into the mold. Alternatively, the porous substrate may be placed in the mold prior to introduction of the hydrogel material.

The porous substrate can be any substantially open-celled, or reticulated net-like material which does not adversely effect the hydrogel material. In addition, various other materials may also be bonded to the porous substrate prior to contact with the hydrogel mixture. For example, cloths such as terrycloth may be bonded to a sheet of urethane foam, thereby allowing the formation of an object having a layer of hydrogel material securely bonded to sheet of urethane foam and having a terrycloth outer covering.

Further, in accordance with the present invention, a method is provided for forming objects having a core material comprising a substituted urea/urethane hydrogel material.

The components of the hydrogel material comprise from about 10 to 20 percent by weight prepolymer, from about 10 to 60 percent by weight polyol and from about 20 to 80 parts by weight water. Most preferably the prepolymer is present in an amount of about 12 to 16 percent by weight, with the polyol and water being present in an amount of about 40 to 50 percent by weight.

Generally, it is preferred that cold water be utilized in preparing the hydrogel in order to slow the rate of reaction (gel formation). After the cold water is added to the reaction vessel, the mixture is quickly poured into an appropriate mold. This is preferably done within about thirty seconds of adding the water to the reaction vessel. Shortly after the hydrogel mixture is introduced into the desired mold, a sheet of substantially open-celled foam substrate is placed in contact with the mixture. As the hydrogel mixture begins to gel, carbon dioxide is liberated therefrom and escapes into the sheet of foam material. In this manner, the froth which generally forms on the uppermost surface of the hydrogel material is actually incorporated into the sheet of foam. Additionally, the sheet of foam substrate is bonded to the hydrogel material as the material gels.

After the hydrogel material has substantially completely set up, it can be removed from the mold. This can be done by lifting the sheet of foam substrate to which the hydrogel has now become bonded. It is preferred that the foam substrate have a layer of cloth, such as terrycloth, bonded to one side thereof. In this manner, one can form an object having an outermost layer of terrycloth bonded to a foam substrate which has been integrally bonded to a hydrogel material. One can then attach the outermost edges of the terrycloth material to form a desired object. Such objects can include a simple square or rectangular-shaped hot or cold compress, or may comprise other objects such as mittens for warming the hands. Additionally, a stocking cap having a layer of the hydrogel material throughout can be formed and used as a hypothermia cap for minimizing hair loss in cancer patients receiving chemotherapy. Further, medication such as methyl salicylate may be incorporated into the hydrogel material for treatment of muscle strains, sprains, overexertion, fatigue, arthritis and tendonitis.

DETAILED DESCRIPTION

In one aspect, the present invention relates to a method for bonding a substituted urea-urethane hydrogel material to a sheet of a substantially open-celled substrate.

The hydrogel is prepared by combining the polyisocyanate prepolymer with an aqueous reactant containing organic polyol and rapidly mixing the two ingredients until the aqueous reactant is homogeneously dispersed in the form of droplets. The mixture is allowed to complete its gelation to produce the liquid-filled elastomer gel.

In an alternative embodiment, the process is carried out in two stages wherein water is mixed with the polyisocyanate prepolymer in a first stage and gelaton is commenced. After the gelatin is under way, the organic polyol alone or with supplemental water is added to the mixture in a second stage and mixed to disperse the liquids.

Preferably, the prepolymer employs any available diisocyanates or mixture of diisocyanates with polyisocyanates having an NCO value of less than about 2.2 such as toluene diisocyanate, polymethylene-polyphenylenediisocyanate, isophorene diisocyanate, aliphatic diisocyanate mixed with a polyether. Preferably the polyether contains at least 40% by weight ethylene oxide adduct. The mixed quantities of diisocyanate/polyisocyanate and the polymer should be such that the prepolymer should have an excess NCO value of about 3.2% to 3.3%. This value is also affected by the process conditions such as heating.

This value is important since below this amount, the prepolymer typically increases in viscosity to form a premature gel-like material which is difficult if not impossible to use. Above this amount, the final gel does not contain sufficient substituted polyol components to provide the water retention characteristics needed for the hydrogel's performance.

Typical polyols are diols and triols formed by combining ethylene oxide with lower molecular weight diols such as glycerene or a glycol. The polyol may also employ some propylene oxide or butylene oxide or other aliphatic oxides as adducts. The high concentration of ethylene oxide adduct in the polyol ingredient achieves the water retention characteristics which are unique in the present substituted urea/urethane hydrogels. A preferred polyol contains at least about 40 weight percent ethylene oxide adduct. A preferred polyether polyol has a molecular weight of from about 3,000 to about 10,000.

The most preferred diisocyanate prepolymer is a toluene diisocyanate prepolymer having a viscosity at 25° C. Brookfield LVF of 6250 cps; a specific gravity of approximately 1.10 and an excess of 3.2% isocyanates, although other suitable diisocyanate prepolymers may be utilized. Considering the intended use of the finished product, it is prefered that all components of the finished hydrogel be substantially nonirritating and nontoxic.

The process for making the hydrogel material essentially comprises mixing from about 10 to 20% by weight diisocyanate prepolymer with from about 10 to 60% by weight polyol and then adding from about 20 to 80% by weight water. It is preferred that the prepolymer be present in an amount of from about 10 to 18% by weight, with 12 to 16% by weight being most preferred. The polyol is preferably present in an amount of between about 10 to 50% by weight, with about 40 to 50% being most preferred. Finally, the water is preferably present in an amount of between about 40 to 80% by weight, with about 40 to 50% water being most preferred. It is also preferred that the water used be between about 33° F. to 60° F. to slow the gellation reaction. Additionally, colorant may be added to the water or the glycol before mixing if a tint is desired in the finished gelled product.

The final mixture is quickly introduced into an open-face mold where it will gel in approximately 60 seconds. In accordance with the method of the present invention, a sheet of a porous substrate is placed in contact with the mixture prior to the time that complete gel formation has occurred, and is maintained in contact therewith for a sufficient amount of time to allow bonding of the porous substrate to the hydrogel material. Generally, the gelled material can be separated from the mold within approximately three to five minutes.

The porous substrate material is preferably a flexible, stretchable material such as substantially open-celled foams with a polyether or a polyester-based urethane, foam being most preferred. Such foams may be reticulated, that is, the cells of the foam communicate with each other thereby creating a full network through which air or fluids can pass from cell to cell. For application of the foam to the surface of the gel, it is preferred that the hydrogel mixture be allowed to begin gel formation within the mold prior to contacting the mixture with the sheet of porous substrate. Generally, a delay of about 20 seconds will suffice.

When the porous substrate is placed in contact with the mixture, some of the mixture is absorbed into the porous substrate and becomes interdiginated within the reticulated pores therein. Upon gel formation, the hydrogel material becomes bonded to the porous substrate. Further, the froth created by virtue of the carbon dioxide leaving the hydrogel is entrapped within the sheet of porous substrate and not visible.

Further, in accordance with the present invention, a method is provided for forming objects having a layer of a thermally efficient hydrogen material incorporated therein. The hydrogel material is prepared in accordance with the method set forth above, with the hydrogel bonded directly to a sheet of porous substrate. The shape of the mold and of the sheet of porous substrate are such that, after the hydrogel material has gelled sufficiently, it may be removed from the mold by lifting the sheet of porous substrate.

For example, a cloth/porous substrate and hydrogel material can be shaped in the form of a stocking cap. Because of the unique properties of the hydrogel material, the cap may be placed in the freezer for extended periods of time whereupon it will not freeze of become inflexible. The precooled cap may then be used as a hypothermia cap for minimizing hair loss in cancer patients receiving chemotherapy. Further, the cap will remain therapeutically cool for more than one hour under most conditions.

The hydrogel and cloth/porous substrate material may also be configured such that upon removal from the mold, the edges of the cloth/porous substrate may be joined to form a mitten. The mitten can then be warmed and used as a therapeutic arthritic handwarming mitten. Once warmed, the hydrogel material will remain therapeutically warm for more than one hour. Should the articles formed in accordance with the present invention become partially dehydrated, such articles can be rejuvenated by merely placing the article in water for a sufficient period of time.

As is apparent, the hydrogel and terrycloth/urethane foam may be formed in various other shapes to form articles such as elbow pads, headband compresses or simple rectangular-shaped hot or cold compresses. Additionally, medication or other additives may be incorporated into the hydrogel material for specified ailments. For example, methylsalycilate may be incorporated into a hot or cold compress.

To further illustrate the present invention, and not by way of limitation, the following example is provided.

EXAMPLE

Into a glass reaction vessel containing no free water, 0.44 pounds of a toluene diisocyanate prepolymer having a viscosity at 25° C. Brookfield LVF of 6250 cps; a specific gravity of approximately 1.10 and 3.2% isocyanates, is introduced. 600 ml of propylene glycol is then introduced into a clean glass beaker containing no free water. Into a separate, clean beaker, 600 ml of water is introduced. The water temperature is approximately 45° F. The 600 ml of propylene glycol is then addd to the reaction vessel containing the diisocyanate prepolymer and stirred for 10 to 15 seconds until the two components are well mixed. The 600 ml of water containing the colorant is then added to the reaction vessel mixture and stirred for approximately 15 seconds until well mixed. The homogenous mixture in the reaction vessel is then poured into an appropriate mold. After approximately 20 seconds, a sheet of polyurethane foam with or without a layer of cloth onto one side thereof is placed in contact with the homogenous mixture and allowed to remain in contact therewith until gel formation is substantially complete, about 3 minutes. The hydrogel material is then removed from the mold by lifting the sheet of polyurethane foam having the cloth bonded thereto. The edges of the cloth material may be attached to form a shaped hot/cold compress.

While the invention has been described above with respect to its preferred embodiments, it will be understood that the invention is capable of numerous rearrangements, modifications and alterations. For example, it will be seen by one skilled in the art that many shapes and configurations are possible and all such arrangements, modifications and alterations are intended to be within the scope of the appended claims.

We claim:

1. A hot or cold compress comprising a layer of a substituted urea/urethane hydrogel material bonded to first side of a porous substrate and absent the opposing side of said substrate, said layer of hydrogel comprising between approximately 20 to 80% weight water, approximately 10 to 60% by weight of a weight polyol and approximately 10 to 20% by weight of a diisocyanate prepolymer.

2. The compress of claim 1 wherein said water is present in an amount of between about 40 to 50% by weight, said polyol is present in an amount of between about 10 to 50% by weight and said diisocyanate prepolymer is present in an amount between about 10 to 20% by weight.

3. The compress of claim 2 wherein said water and said polyol are present in an amount of between about 40 to about 50% by weight and said diisocyanate prepolymer is present in an amount of between about 12 to 16% by weight.

4. The compress of claim 3 wherein said water and said polyol are present in an amount of about 43% by weight and said diisocyanate prepolymer is present in an amount of about 14% by weight.

5. The compress of claim 1 wherein said porous substrate commprises a substantially open-celled foam material.

6. The compress of claim 1 wherein said porous substrate comprises a polyether-based, recticulated urethane foam.

7. The compress of claim 1 wherein said porous substrate comprises a polyester-based urethane foam.

8. The compress of claim 1 wherein said polyol is selected from the group comprising propylene glycol, dipropylene glycol, ethylene glycol, diethylene glycol or mixtures thereof.

9. The compress of claim 8 wherein the polyol is propylene glycol.

10. The compress of claim 1 wherein the diisocyanate prepolymer comprises a toluene diisocyanate prepolymer.

11. The compress of claim 1 wherein the porous substrate further comprises a layer of cloth bonded to said porous substrate.

12. The compress of claim 1 wherein said compress is configured in the shape of a stocking cap.

13. The compress of claim 1 wherein the compress is configured in the shape of a mitten.

14. The compress of claim 1 wherein said compress is a rectangular solid having means for attaching said compress to a head.

15. The compress of claim 1 wherein said hydrogel material is impregnated with medication.

16. The compress of claim 15 wherein said medication is methylsalycilate and wherein said substrate is configured in the shape of a strap useful for applying said compress to a portion of a wearer's body.

17. A method for forming objects having a substituted urea/urethane hydrogel layer bonded to a first side of a layer of porous substrate and absent the opposing side of said substrate, comprising:
preparing said hydrogel material;
contacting said first side of porous substrate with said hydrogel material prior to complete gel formation of said hydrogel;
maintaining said layer of porous substrate in contact with said hydrogel material until gel formation is substantially complete, thereby bonding said porous substrate material to the hydrogel material; and
forming a desired object from said hydrogel bonded to said porous substrate.

18. The method of claim 17 further comprising introducing said hydrogel material into a mold having a desired shape prior to contacting said porous substrate with said hydrogel.

19. The method of claim 17 wherein said hydrogel is prepared by mixing between approximately 10 to 20% by weight of a diisocyanate prepolymer with approximately 10 to 60% by weight of a high molecular weight polyol, and then adding between approximately 20 to 80% by weight water to said diisocyanate/polyol mixture.

20. The method of claim 19 wherein said diisocyanate prepolymer is present in an amount of between about 10 to 20% by weight, said polyol is present in an amount of between about 10 to 50% by weight and said water is present in an amount of between about 40 to 50% by weight.

21. The method of claim 19 wherein said prepolymer is present in an amount of between about 12 to 15% by weight and said water and said polyol are present in an amount of between about 40 to 50% by weight.

22. The method of claim 19 wherein said prepolymer is present in an amount of about 14% by weight and said water and said polyol are present in an amount of approximately 43% by weight.

23. The method of claim 17 wherein said porous substrate comprises a substantially open-celled foam material.

24. The method of claim 17 wherein said porous substrate comprises a urethane foam.

25. The method of claim 17 wherein said porous substrate is a polyether-based, recticulated urethane foam.

26. The method of claim 17 wherein said porous substrate is a polyester-based urethane foam.

27. The method of claim 19 wherein said polyol is selected from the group comprising propylene glycol, dipropylene glycol, ethylene glycol, diethylene glycol, or mixtures thereof.

28. The method of claim 27 wherein said polyol is propylene glycol.

29. The method of claim 19 wherein said diisocyanate prepolymer comprises a toluene diisocyanate prepolymer.

30. The method of claim 17 wherein said porous substrate further comprises a cloth material bonded thereto.

31. The method of claim 30 wherein said cloth material is terrycloth.

32. The method of claim 17 wherein the desired object is a stocking cap.

33. The method of claim 17 wherein the object is a mitten.

34. The method of claim 17 wherein the object is a rectangular solid having means for attaching said rectangular solid to a head.

35. The method of claim 17 further comprising impregnating said hydrogel material with medication.

36. The method of claim 35 wherein said medication is methylsilicylate.

37. The product formed by the process recited in claim 17.

38. The product formed by the process recited in claim 19.

39. The product formed by the process recited in claim 22.

40. A method for bonding a substituted urea/urethane hydrogel material to a first side of a porous substrate material and absent the opposing side of said substrate comprising:
contacting said porous substrate material with said hydrogel material prior to the time that said hydrogel material has completely gelled; and
maintaining said porous substrate in contact with said hydrogel material until gel formation of the hydrogel is substantially complete, thereby bonding the porous substrate to the hydrogel material.

41. The method of claim 40 wherein said porous substrate material comprises a substantially open-celled foam.

42. The method of claim 40 wherein the porous substrate is a polyether-based, recticulated foam.

43. The method of claim 40 wherein the foam is a polyester-based urethane foam.

44. The method of claim 40 wherein said form has a layer of cloth material bonded thereto.

45. The method of claim 44 wherein said cloth material is flame bonded to said foam.

* * * * *